United States Patent [19]

Wakselman et al.

[11] Patent Number: 5,082,945
[45] Date of Patent: Jan. 21, 1992

[54] PROCESS FOR THE PREPARATION OF PERHALOALKYLTHIOETHERS

[75] Inventors: Claude Wakselman, Paris; Marc Tordeux, Sceaux; Bernard Langlois, Lyons; Jean-Louis Clavel, Ecully; Roland Nantermet, Lyons, all of France

[73] Assignee: Rhone-Poulenc Agrochimie, Lyons, France

[21] Appl. No.: 448,983

[22] Filed: Dec. 12, 1989

[30] Foreign Application Priority Data

Dec. 13, 1988 [FR] France .................. 88 16710
Oct. 9, 1989 [FR] France .................. 89 13371

[51] Int. Cl.$^5$ .................... C07D 231/14; C07C 49/16
[52] U.S. Cl. .................................... 548/110; 546/276; 548/376; 548/378; 568/38; 568/56; 568/59
[58] Field of Search ............... 568/56, 59, 38; 546/276; 548/110, 376, 378

[56] References Cited

U.S. PATENT DOCUMENTS 3,506,718  4/1970  Mutsch .................. 568/56

FOREIGN PATENT DOCUMENTS 0234119  9/1987  European Pat. Off. .......... 548/377

OTHER PUBLICATIONS

Reid, *Organic Chemistry of Bivalent Sulfur*, vol. III, Chapter 7, 1960, pp. 362-386.

*Primary Examiner*—C. Warren Ivy
*Assistant Examiner*—Zinna Northington-Davis
*Attorney, Agent, or Firm*—Burns, Doane, Swecker & Mathis

[57] ABSTRACT

The present invention relates to a process for the preparation of perhaloalkylthioethers by bringing a perhaloalkyl halide, preferably a bromide or an iodide, into contact with a disulphide in the presence of zinc and of sulphur dioxide or of a dithionite or of a hydroxymethanesulphinate or of a formate anion and sulphur dioxide.

16 Claims, No Drawings

PROCESS FOR THE PREPARATION OF PERHALOALKYLTHIOETHERS

The present invention relates to a process for the preparation of perhaloalkylthioethers; it relates more particularly to the preparation of perhaloalkylthioethers by reaction of a disulphide with a perhaloalkane in the presence of a reducing agent.

Various processes allowing perhaloalkylthioethers to be obtained are known in the prior art. There is known, in particular, J. gen. Chem. USSR 1952, 22, 2273 and 1954, 24, 885, which describe the preparation of various trifluoromethylthiobenzenes by chlorination of the corresponding —$SCH_3$ derivative to a —$SCCl_3$ derivative, followed by fluorination of the latter to —$SCF_3$. This same method makes it possible, by incomplete fluorination, to obtain the —$SCF_2Cl$ derivatives (see Angew. Chem. Int. Ed., 1977, 16, 735).

It is also possible to mention J. Org. Chem. 1964, 29, 895, which describes the condensation of trifluoromethanesulphenyl chloride $CF_3SCl$ with organomagnesium compounds to obtain the —$SCF_3$ derivatives.

Synthesis 1975, 721 describes a process for the preparation of —$SCF_3$ derivatives by reaction of $CF_3SCu$ with the corresponding iodide.

Another process of the prior art consists in reacting $CF_3I$ and a thiol under ultraviolet irradiation in liquid ammonia (J. Org. Chem. USSR 1977, 13, 972).

Finally, there will be mentioned the preparation of $SCF_2BR$ derivatives by the action of $CF_2Br_2$ or $CF_2BrCl$ on thiophenates in liquid-liquid phase transfer conditions, the phase transfer agent being a quaternary ammonium salt (Tetrahedron Letters 1981, 22, 323).

This last process does not permit the use of $CF_3Br$ and of $CF_2Cl_2$ and hence does not allow the preparation of the —$SCF_3$ and $SCF_2Cl$ derivatives.

The other processes mentioned exhibit disadvantages which are relatively incompatible with an industrial application and which are, chiefly, the large number of stages which are necessary, the use of costly and/or toxic products such as $CF_3I$, $CF_3SCl$ and $CF_3SCu$, the intermediate use of an organomagnesium compound, of whose disadvantages a person skilled in the art is well aware, or else the use of reactions in liquid ammonia.

Patent FR 2,540,108 concerns solely the preparation of phenylperfluoroalkyl sulphides by reaction of thiophenates on perfluoroalkyl halides. This method involves the preliminary formation of oxidizable thiophenates.

Patents EP 201,852 and 234,119 should also be notes (especially EP 201,852, pages 45 and 61-62), which describe the reaction of alkyl halide with the disulphide in the presence of alkali metal dithionite. However, this method requires the preliminary preparation of the thiolate and experience has shown that this method is not valid in the case of perfluoroalkyl halides.

None of the processes described in the prior art is capable of industrial application. Industry is looking, in fact, for a relatively inexpensive and especially nonhazardous process for obtaining perhaloalkyl sulphides, requiring a minimum number of synthesis stages.

The present invention corresponds to this objective and its subject is more particularly a process for the preparation of perhaloalkylthioethers by bringing into contact, optionally in a solvent, a reducing agent consisting of a metal chosen from zinc, cadmium, aluminium and manganese, with sulphur dioxide, or consisting of an alkali metal dithionite or of an alkali or alkaline-earth metal or metal hydroxymethanesulphinate or consisting of a formate an ion and of sulphur dioxide, a disulphide, and a perfluoroalkyl halide.

The perhaloalkylthioethers correspond to the following general formula:

$$R S C F Y T \qquad\qquad I$$

in which:

R denotes an optionally substituted hydrocarbyl group

Y and T denote independently a halogen chosen from fluorine, chlorine and bromine or a perhaloalkyl chain containing 1 to 11 carbon atoms.

A perhaloalkyl chain means a chain in which all the hydrogen atoms have been replaced by chlorine and/or bromine and/or fluorine atoms and in which the chlorine and/or bromine atoms are not vicinal.

They are obtained by reaction of a disulphide and of a perfluoroalkyl halide according to the following reaction:

In this process, the perfluoroalkyl halides correspond to the formula:

$$X C F Y T \qquad\qquad II$$

in which

X denotes a halogen chosen from Cl, Br and I,

Y and Y have the same meaning as in formula (I).

Compounds of formula II which may be mentioned are trifluoromethyl bromide, perfluoroethyl iodide, 1,1,2-trichlorotrifluoroethane, trichlorofluoromethane, 1,1,1-trichlorotrifluoroethane, dibromodifluoromethane and dichlorodifluoromethane.

Preferably, when X denotes chlorine, Y cannot denote fluorine nor a perfluoroalkyl chain.

Preferably, when X denotes bromine, Y and T denote fluorine, and when X denotes iodine, Y denotes a perfluoroalkyl chain, and T a fluorine atom.

A hydrocarbyl group is intended to denote especially:

A linear or branched carboacyclic (aliphatic) group containing one to five ethylenic or acetylenic unsaturations but, preferably, saturated;

A carbocyclic or heterocyclic group chosen from an aromatic or nonaromatic (preferably saturated) monocyclic system, an aromatic or nonaromatic (preferably saturated) bicyclic system, an aromatic or nonaromatic (preferably saturated) polycyclic system, or a bridged (preferably saturated) system.

When the term polyhalo is employed in the case of a saturated substituent, it means that the halogens are not vicinal, with the exception of fluorine.

In the case of the carboacyclic (aliphatic) groups, the permissible substituents (Z) are identical or different and are chosen from halogen atoms (I, Cl, Br, F); $C_6$-$C_{10}$ aryl radicals optionally substituted by 1 to 6 substituents chosen from halogen atoms (I, Cl, Br, F), $C_1$-$C_6$ alkyl, $C_1$-$C_6$ alkoxy, $C_1$-$C_6$ alkylthio, polyhalo-$C_1$-$C_6$-alkyl, polyhalo-$C_1$-$C_6$-alkoxy, polyhalo-$C_1$-$C_6$- alkylthio, $C_1$-$C_6$ alkylsulphinyl, polyhalo-$C_1$-$C_6$-alkylsulphinyl, cyano, $C_1$-$C_6$ alkylsulphonyl or polyhalo-$C_1$-$C_6$-alkylsulphonyl, $C_1$-$C_6$ alkoxycarbonyl, and polyhalo-$C_1$-$C_6$-alkoxycarbonyl radicals; $C_1$-$C_6$ alkylcarbonyloxy; polyhalo-$C_1$-$C_6$-alkylcarbonyloxy; an $S(O)_m$-$R_1$ residue in which $R_1$ is an amino, $C_1$-$C_6$ alkylamino, di($C_1$-$C_6$-alkyl)amino, polyhalo-$C_1$-$C_6$-alkylamino or di(polyhalo-$C_1$-$C_6$-alkyl)amino group and m=0, 1 or 2; $C_1$-$C_9$ heteroalkyl radicals additionally containing 1 to 4 heteroatoms chosen from nitrogen, sulphur and oxygen, optionally substituted by one of the substituents defined above in the case of the $C_6$-$C_{10}$ aryl radicals; $C_1$-$C_6$ alkoxy radicals; polyhalo-$C_1$-$C_6$-alkoxy; $C_1$-$C_6$ alkylthio; polyhalo-$C_1$-$C_6$-alkylthio; $C_1$-$C_6$ alkylsulphinyl; polyhalo-$C_1$-$C_6$-alkylsulphinyl; $C_1$-$C_6$ alkylsulphonyl; polyhalo-$C_1$-$C_6$-alkylsulphonyl; $C_1$-$C_6$ alkoxycarbonyl; polyhalo-$C_1$-$C_6$-alkoxycarbonyl; $C_1$-$C_6$ alkylcarbonyloxy; polyhalo-$C_1$-$C_6$-alkylcarbonyloxy; hydroxyl; thiol; an $NR_4R_5$ amino group in which $R_4$ and $R_5$, which are identical or different, denote a hydrogen atom; a $C_1$-$C_6$ alkyl group optionally substituted by a $C_2$-$C_5$ alkoxycarbonyl group; $C_3$-$C_6$ cycloalkyl; $C_2$-$C_7$ alkanoyl, optionally forming a cyclic imide group of 5 to 6 atoms together with the nitrogen atom to which they are attached, it being possible for the said groups to be optionally substituted by one to six halogen atoms; $C_2$-$C_7$ alkoxycarbonyl; polyhalo-$C_2$-$C_7$-alkoxycarbonyl; Z also denotes $C_2$-$C_5$ alkoxymethylene optionally substituted on the methylene by a $C_1$-$C_4$ alkyl group; carboxytri($C_1$-$C_6$-alkyl)silylmethyl; tri($C_1$-$C_6$-alkyl)silyl; cyano; Z also denotes an HN—C(=A)—$R_6$ residue, $R_6$ being a hydrogen atom, a $C_1$-$C_6$ alkyl radical; $C_2$-$C_4$ alkenyl; $C_2$-$C_4$ alkynyl; $C_1$-$C_4$ alkoxyalkyl, $C_1$-$C_4$ alkylthioalkyl, $C_1$-$C_4$ alkoxy; $C_1$-$C_4$ alkylthio, $C_1$-$C_4$ alkylamino, di($C_1$-$C_4$-alkyl)amino; polyhalo-$C_1$-$C_4$-alkyl; $C_3$-$C_7$ cycloalkyl, optionally substituted by one or more halogen atoms or $C_1$-$C_4$ alkyl; $C_1$-$C_4$ haloalkyl or $R_6$ also denotes a phenyl nucleus; phenylthio; phenoxy; phenylamino, it being possible for these phenyl nuclei to be optionally substituted by cyano, $C_1$-$C_4$ alkyl or $C_1$-$C_4$ alkoxy radicals; $C_1$-$C_4$ alkylthio; $C_1$-$C_4$ alkylsulphinyl; $C_1$-$C_4$ alkylsulphonyl; polyhalo-$C_1$-$C_4$-alkyl; polyhalo-$C_1$-$C_4$-alkoxy; polyhalo-$C_1$-$C_4$-alkylthio; polyhalo-$C_1$-$C_4$-alkylsulphinyl; polyhalo-$C_1$-$C_4$-alkylsulphonyl; Z may also denote a $C_3$-$C_7$ cycloalkyl or polyhalo-$C_3$-$C_7$-cylcoalkyl radical or a $C_1$-$C_4$ alkylsulphenylamino radical.

A is a sulphur or oxygen atom.

The permissible substituents Z are preferably chosen from the following substituents:

halogen atoms (I, Cl, Br, F); $C_6$-$C_{10}$ aryl radicals, optionally substituted by 1 to 6 substituents chosen from halogen atoms (I, Cl, Br, F), $C_1$-$C_6$ alkyl, $C_1$-$C_6$ alkoxy, polyhalo-$C_1$-$C_6$-alkyl or polyhalo-$C_1$-$C_6$-alkoxy radicals; the $C_1$-$C_9$ heteroaryl radicals additionally containing 1 to 4 heteroatoms chosen from nitrogen, sulphur and oxygen, optionally substituted by one of the substituents defined above in the case of the $C_6$-$C_{10}$ aryl radicals; $C_1$-$C_6$ alkoxy radicals; polyhalo-$C_1$-$C_6$-alkoxy, cyano, amino; $C_1$-$C_6$ alkyl; polyhalo-$C_1$-$C_6$-alkyl.

In the case where R is a carbocyclic or heterocyclic radical, the substituents Z are the same as in the case of the carboacyclic radicals and can additionally correspond to $C_1$-$C_6$ alkyl radicals; polyhalo-$C_1$-$C_6$-alkyl.

In this latter case the substituents are preferably the same as in the case of the preferred substituents of the carboacyclic radicals but can additionally correspond to $C_1$-$C_6$ alkyl radicals; polyhalo-$C_1$-$C_6$-alkyl.

The radicals R normally number 0 to 6 substituents Z and within the scope of this description the term polyhalo corresponds to 1 to 6 halogen atoms. Moreover, unless specified otherwise, the alkyl radicals in general (including alkoxy, alkylthio, and the like) are linear or branched.

The acyclic groups preferably contain 1 to 24 carbon atoms.

The monocyclic systems preferably can be denoted by the formula

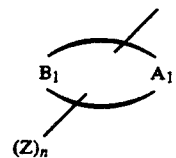

III in which $B_1$ denotes a saturated or unsaturated carbon and $A_1$ denotes an atom chain which, together with $B_1$, forms a monocyclic system containing from 0 to 3 double bonds or 0 to 2 triple bonds. $A_1$ may comprise 2 to 12 carbon atoms or may comprise a combination of 1 to 11 carbon atoms and 1 to 4 heteroatoms which may be chosen independently from N, O, S, P or another heteroatom or may contain 4 single heteroatoms forming a ring with $B_1$.

The systems comprising heteroatoms can in some cases carry oxygen atoms as in aromatic systems containing an N-oxide group or containing a sulphinyl, sulphonyl, selenoxide and phosphine oxide group.

Certain carbons of the rings formed by $A_1$ and $B_1$ may carry carbonyl, thiocarbonyl, methylidene, oxime or imino groups optionally substituted by $C_1$-$C_6$ alkyl, $C_3$-$C_8$ cycloalkyl or $C_6$-$C_{10}$ aryl groups, the said groups being optionally substituted by one to 6 groups Z such as defined above.

The group indicated by Z denotes one or more substituents chosen independently from the group of substituents defined above in the case of Z. In general n=0 to 6.

The bicyclic systems may be denoted by the formulae:

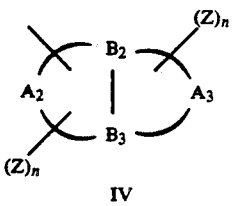 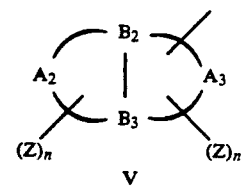

IV    V in which $B_2$ and $B_3$ can be independently a saturated or unsaturated carbon atom or a nitrogen atom, $A_2$ and $A_3$ independently denote a chain of atoms described below and Z denotes one or more substituents chosen independently from the group of substituents defined above in the case of Z. The $A_2$ and $A_3$ groups may, in combination with $B_2$ or $B_3$, contain from 0 to 5 double bonds. $A_2$ and $A_3$, independently of $B_2$ and $B_3$, may contain from 1 to 3 heteroatoms which may be chosen from N, O, S, P or other heteroatoms together with 1 to 10 carbon atoms or may contain from 1 to 3 single heteroatoms forming the ring.

In certain cases the heteroatoms may carry oxygen atoms as in N-oxide aromatic rings and systems containing sulphinyl, sulphonyl, selenoxide and phosphine oxide groups. Certain carbon atoms may be carbonyl or thiocarbonyl groups, imine or methylidene or oxime groups, these groups being optionally substituted by a $C_1$–$C_{12}$ alkyl, $C_3$–$C_8$ cycloalkyl, or $C_6$–$C_{10}$ aryl group, which are optionally substituted by one to 6 groups Z such as defined above.

The groups Z in formulae IV and V are identical or different and their number is such that n is between 0 and 6 (n being identical or different in the case of each ring).

With regard to the structures included by IV and V, it should be noted that:

a) When $B_2$ and $B_3$ correspond to the nitrogen atom, the groups $A_2$ and $A_3$ must not contain fewer than 3 atoms each.

b) When $B_2$ but not $B_3$ is the nitrogen atom either $A_2$ or $A_3$ should contain at least 3 atoms and the other at least two.

c) When either $A_2$ or $A_3$ contains fewer than 3 atoms, the other contains at least 3 atoms and the bridge must be saturated.

d) When the group $A_2$ or $A_3$ contains a carbon atom carrying a carbonyl, thionyl, imino or methylidene or oxime, it must, together with $B_2$ and $B_3$, form a ring which has at least four members.

e) When an annular double bond is exocyclic to one of the two rings, it must be included in a ring containing at least five members or be exocyclic to the ring containing at least five member.

f) When a chain link $A_2$ or $A_3$ is attached to the bridge atoms $B_2$ and $B_3$ by two double bonds, the group $A_2$ or $A_3$ is understood to include a double bond and the bridge atoms are considered as being unsaturated.

It should be understood that the bicyclic systems may be spirocyclic.

The polycyclic systems which have more than two rings may be denoted by the formulae:

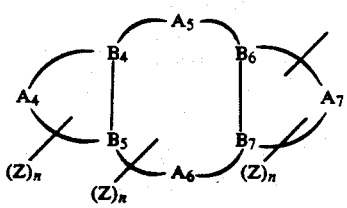

VI

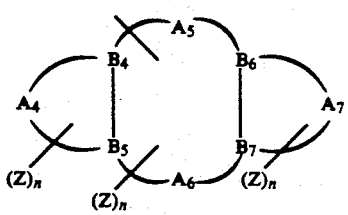

VII

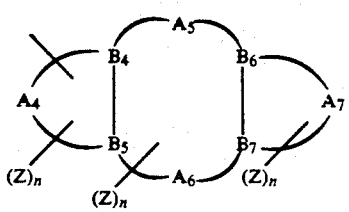

VIII

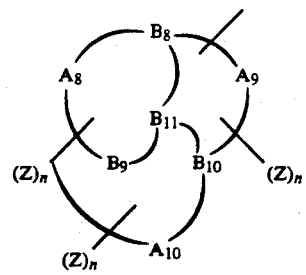

IX in which $B_4$, $B_5$, $B_6$ and $B_7$ may independently be a saturated or unsaturated carbon atom or a saturated nitrogen atom and $A_4$, $A_5$, $A_6$ and $A_7$ independently denote chains of atoms which may contain together with either (but not both) of their bridged atoms associated with 0 to 2 double bonds. The groups Z are identical to those indicated above.

$A_4$, $A_5$, $A_6$ and $A_7$, independently of $B_4$, $B_5$, $B_6$ and $B_7$, may contain from 1 to 11 carbon atoms or could contain a combination of 1–10 carbon atoms and of 1 to 3 heteroatoms chosen independently from N, O, S, P or other heteroatoms or could contain 1 to 3 single heteroatoms.

In certain cases the heteroatoms may carry oxygen atoms as in N-oxide aromatic rings and systems containing sulphinyl, sulphonyl, selenoxide and phosphine oxide groups. Certain carbon atoms may be carbonyl or thiocarbonyl groups, imine or methylidene or oxime groups optionally substituted by a $C_1$–$C_{12}$ alkyl, $C_3$–$C_8$ cycloalkyl or $C_6$–$C_{10}$ aryl group, these groups being optionally substituted by one to six groups Z such as defined above.

The groups Z in formulae VI to IX are identical or different and their number is such that n is between 0 and 6 (n being identical or different in the case of each ring). With regard to the structure IX, the groups $B_8$, $B_9$ and $B_{10}$ denote independently a saturated or unsaturated carbon atom or a saturated nitrogen atom.

Group $B_{11}$ may denote a saturated or unsaturated carbon atom or a nitrogen or phosphorus atom.

Groups $A_8$, $A_9$ and $A_{10}$ denote atom chain links which, together with 1 of the groups $B_8$, $B_9$, $B_{10}$ and $B_{11}$, may contain from 0 to 2 double bonds. The chain links of groups $A_8$, $A_9$ and $A_{10}$, independently of groups $B_8$, $B_9$, $B_{10}$ and $B_{11}$, may contain from 2 to 10 carbon atoms or 1 to 10 carbon atoms in combination with 1 to 3 heteroatoms chosen from N, O, S, P or others or may contain from 2 to 3 single heteroatoms. In certain cases the heteroatoms may carry oxygen atoms as in N-oxide aromatic rings and systems containing sulphinyl, sulphonyl, selenoxide and phosphine oxide groups. Certain carbon atoms may be carbonyl or thiocarbonyl groups or imine or methylidene or oxime groups, these groups being optionally substituted by a $C_1$–$C_{12}$ alkyl, $C_3$–$C_8$ cycloalkyl or $C_6$–$C_{10}$ aryl group, which are optionally substituted by one to six groups Z such as defined above.

The groups Z in formula IX are identical or different and their number is such that n is between 0 and 6 (n being identical or different in the case of each ring).

It should be noted that the polycyclic groups may be spirocyclic, saturated or unsaturated, and optionally substituted by one or more substituents Z indicated above and n=1 to 6 with the stipulation that n is identical or different in the case of each ring.

The bridged bicyclic systems may be denoted by the generalized formulae

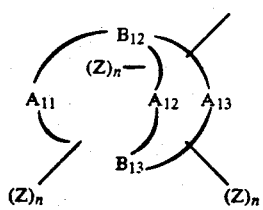 X

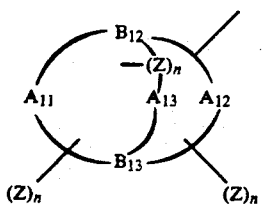 XI

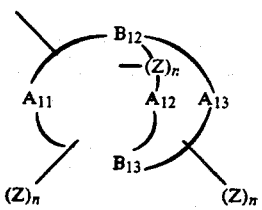 XII in which $B_{12}$ and $B_{13}$ may be independently a saturated carbon atom optionally substituted by one of the groups Z or a nitrogen atom, and the groups $A_{11}$, $A_{12}$ and $A_{13}$ independently denote chain links of atoms which, independently of $B_{12}$ and $B_{13}$, may contain from 0 to 2 double bonds.

The chain links $A_{11}$, $A_{12}$ and $A_{13}$, independently of $B_{12}$ and $B_{13}$, may contain 1-11 carbon atoms or 1 to 10 carbon atoms and 1-3 heteroatoms which may be chosen independently from N, O, S, P or others or may contain 1-3 single heteroatoms, with the condition that when one of the chain links $A_{11}$, $A_{12}$ and $A_{13}$ is a single heteroatom the other two chain links must comprise at least 2 atoms, a second condition being that, when one or both chain links $B_{12}$ and $B_{13}$ are the nitrogen atom, the chain links $A_{11}$, $A_{12}$ and $A_{13}$ must contain at least two saturated atoms.

In certain cases the heteroatoms may carry oxygen atoms as in N-oxide aromatic rings and systems containing sulphinyl, sulphonyl, selenoxide and phosphine oxide groups. Certain carbon atoms may be carbonyl or thiocarbonyl groups or imine or methylidene or oxime groups, these groups being optionally substituted by a $C_1-C_{12}$ alkyl, $C_3-C_8$ cycloalkyl or $C_6-C_{10}$ aryl group, which are optionally substituted by one to six Z groups such as defined above.

The groups Z in the formula X, XI and XII are identical or different and their number is such that n is between 0 and 6 (n being identical or different in the case of each ring).

This process is particularly adapted to obtaining compounds from disulphides where R is a phenyl radical optionally substituted by one or more radicals chosen from the following radicals:

halogen atoms (I, Cl, Br, F); $C_6-C_{10}$ aryl radicals optionally substituted by 1 to 6 substituents chosen from halogen atoms (I, Cl, Br, F), $C_1-C_6$ alkyl, $C_1-C_6$ alkoxy, polyhalo-$C_1-C_6$-alkyl or polyhalo-$C_1-C_6$-alkoxy radicals; $C_1-C_9$ heteroaryl radicals additionally containing 1 to 4 heteroatoms chosen from nitrogen, sulphur and oxygen optionally substituted by one of the substituents defined above in the case of the $C_6-C_{10}$ aryl radicals; $C_1-C_6$ alkoxy radicals; polyhalo-$C_1-C_6$-alkoxy and $C_1-C_6$ alkyl or $C_1-C_6$ polyhaloalkyl, cyano or amino radicals.

This process is particularly adapted to obtaining compounds from disulphides where R is an alkyl radical optionally substituted by one or more radicals chosen from the following radicals:

halogen atoms (I, Cl, Br, F); $C_6-C_{10}$ aryl radicals optionally substituted by 1 to 6 substituents chosen from halogen atoms (I, Cl, Br, F), $C_1-C_6$ alkyl, $C_1-C_6$ alkoxy, polyhalo-$C_1-C_6$-alkyl and polyhalo-$C_1-C_6$ alkyl, alkoxy radicals; the $C_1-C_9$ heteroaryl radicals additionally containing 1 to 5 heteroatoms chosen from nitrogen, sulphur and oxygen optionally substituted by one of the substituents defined above in the case of the $C_6-C_{10}$ aryl radicals; $C_1-C_6$ alkoxy radicals; polyhalo-$C_1-C_6$-alkoxy, cyano and amino.

This process is particularly adapted to the preparation of pyrazoles in which R corresponds to the formula:

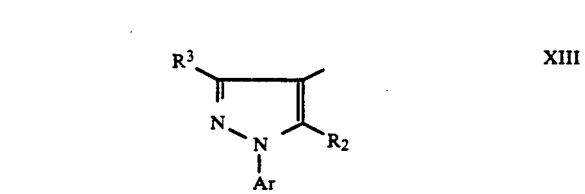 XIII $R_2$ denotes an $NR_4R_5$ amino group in which $R_4$ and $R_5$, which are identical or different denote a hydrogen atom; a $C_1-C_6$ alkyl group optionally substituted by a $C_2-C_5$ alkoxycarbonyl group; $C_3-C_6$ cycloalkyl; $C_2-C_7$ alkanoyl optionally forming a cyclic imide group of 5 to 6 atoms together with the nitrogen atom to which they are attached, it being possible for the said groups to be optionally substituted by one to six halogen atoms; $C_2-C_7$ alkoxycarbonyl; polyhalo-$C_2-C_7$-alkoxycarbonyl; $R_2$ also denotes a $C_1-C_4$ alkylsulphenylamino group; $C_2-C_5$ alkoxymethyleneamino optionally substituted on the methylene by a $C_1-C_4$ alkyl group; a halogen atom; a $C_1-C_5$ alkyl group; carboxy $C_1-C_6$ alkylthio; polyhalo-$C_1-C_6$-alkylthio; $C_1-C_6$ alkylsulphinyl; polyhalo-$C_1-C_6$-alkylsulphinyl, $C_1-C_6$ alkylsulphonyl, polyhalo-$C_1-C_6$-alkylsulphonyl; tri($C_1-C_6$-alkyl)silylmethyl; tri($C_1-C_6$-alkyl)silyl; cyano; hydroxyl; hydroxy-$C_1-C_6$-alkylamino; $C_1-C_6$ alkoxy.

$R_2$ also denotes the hydrogen atom, an HN—C(=A)—$R_6$ residue, $R_6$ being a hydrogen atom or a $C_1-C_6$ alkyl radical; $C_2-C_4$ alkenyl; $C_2-C_4$ alkynyl; $C_1-C_4$ alkoxyalkyl, $C_1-C_4$ alkylthioalkyl, $C_1-C_4$ alkoxy; $C_1-C_4$ alkylthio, $C_1-C_4$ alkylamino, di($C_1-C_4$-alkyl)amino; polyhalo-$C_1-C_4$-alkyl; $C_3-C_7$ cycloalkyl optionally substituted by one or more halogen atoms, $C_1-C_4$ alkyl; $C_1-C_4$ haloalkyl or $R_6$ also denotes a phenyl nucleus; phenylthio; phenoxy; phenylamino, these phenyl nuclei being optionally substituted by cyano, $C_1-C_4$ alkyl or $C_1-C_4$ alkoxy radicals; $C_1-C_4$ alkylthio; $C_1-C_4$ alkylsulphinyl; $C_1-C_4$ alkylsulphonyl; polyhalo-$C_1-C_4$-alkyl; polyhalo-$C_1-C_4$-alkoxy; polyhalo-$C_1-C_4$-alkylthio; polyhalo-$C_1-C_4$- alkylsulphinyl; polyhalo-$C_1-C_4$-alkylsulphinyl; halogen atoms.

A is a sulphur or oxygen atom.

$R_3$ is a halogen atom; hydrogen; a cyano; nitro; COO—$C_1$-$C_6$-alkyl; or $C_1$-$C_6$alkyl group; polyhalo-$C_1$-$C_6$-alkyl; $C_3$-$C_6$cycloalkyl.

Ar is a phenyl or pyridyl nucleus optionally substituted by 1 to 4 substituents chosen from cyano, $C_1$-$C_4$ alkyl or $C_1$-$C_4$ alkoxy radicals; $C_1$-$C_4$ alkylthio; $C_1$-$C_4$ alkylsulphinyl; $C_1$-$C_4$ alkylsulphonyl; polyhalo-$C_1$-$C_4$-alkyl; polyhalo-$C_1$-$C_4$-alkoxy; polyhalo-$C_1$-$C_4$-alkylthio; polyhalo-$C_1$-$C_4$-alkylsulphinyl; polyhalo-$C_1$-$C_4$-alkylsulphonyl; halogen atoms.

These last pyrazole disulphides are described in European Patent Applications No. 0,201,852 and 0,234,119.

To prepare these disulphides, a person skilled in the art will find it useful to refer to the description of these two documents.

This process is very advantageously adapted for the preparation of compounds in which R corresponds to the formula

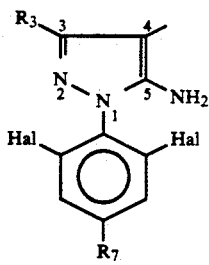

in which:

$R_3$ has the same meaning as above,

Hal is a fluorine, bromine or chlorine atom or is a hydrogen atom, and $R_7$ is a trifluoromethyl, trifluoromethoxy or halogen group.

Among the compounds of formula (II) it is preferred to employ the perfluoroalkyl bromide when the alkyl chain contains a single carbon atom and perfluoroalkyl iodides when the alkyl chain contains at least two atoms.

In fact, trifluoromethyl bromide is a fire-extinguishing gas (M. R. C. Gerstenberger, A. Hass, Angew. Cem. Int. Ed. 1981, 20, 647), which is an industrial product manufactured on a large scale, and therefore with a cost which is quite accessible to industry. Trifluoromethyl iodide, not being industrial, is available only at a price which makes it difficult to employ. On the other hand, as soon as the alkyl chain contains at least 2 atoms, perfluoroalkyl iodides appear on the market at prices which are well below those of their brominated homologues.

The solvent chosen must, as much as possible, permit the dissolution of the dithionite or hydroxymethanesulphinate and the perfluoroalkyl halide.

Polar solvents fulfil this condition and, among these, preferably:
formamide
dimethylformamide (DMF)
dimethylacetamide (DMA)
hexamethylphosphoramide (HMPA)
N-methylpyrrolidone (NMP)
dimethyl sulphoxide (DMSO)
sulpholane
ethers such as dioxane, tetrahydrofuran and dimethoxyethane.

Among the amides it is very particularly preferred to employ dimethylformamide.

Agents capable of producing the formation of CFYT free radicals from XCFYT are referred to as a reducing agent.

According to a first alternative form, the agents employed will be metals chosen from the group consisting of zinc, cadmium, aluminium and manganese, mixed with sulphur dioxide, dithionites and hydroxymethanesulphinates.

Among the metals which are the subject of the process according to the invention the use of zinc is preferred.

The alkali or alkaline-earth metal or metal dithionite preferably corresponds to the general formula (XV) $M_n(S_2O_4)$ in which n is equal to 1 or 2, depending on the valency of metal M.

Among the compounds of formula (XV) it is preferred to employ sodium or potassium dithionite. The use of sodium dithionite is very particularly preferred.

Among the hydroxymethanesulphinates it is preferred to employ sodium hydroxymethanesulphinate (better known under the trade name of Rongalite) or zinc hydroxymethanesulphinate (better known under the trade name of Decroline).

When a dithionite of general formula (XV) or a hydroxymethanesulphinate is employed, a base is advantageously added, chosen from alkali or alkaline-earth metal hydroxides, aqueous ammonia, tris-3,6-dioxaheptylamine, triethylbenzylammonium chloride, salts of weak acids such as, for example, disodium phosphate, sodium metabisulphite, sodium hydrogen sulphite or sodium borate. The use of disodium phosphate is preferred. The quantity of base employed varies advantageously according to a molar ratio of between 0.3 and 3, calculated relative to the disulphide.

The molar quantity of zinc or of dithionite or hydroxymethanesulphinate employed relative to the disulphide is especially greater than 1 and more preferably between 1 and 3.

According to a second alternative form which is also the preferred alternative form, the $SO_2$/formate anion mixture will be employed.

The formate anions advantageously originate from the formates of formula:

$$(HCOO^-)_n R_1^{n+}$$

$R_1^{n+}$, n being equal to 1 or 2, being chosen from the cations of an alkali metal (Na, K, Li), alkaline-earth metal (Ca), ammonium of formula $NR_2R_3R_4R_5$, $R_2$, $R_3$, $R_4$ and $R_5$ being chosen from the hydrogen atom and $C_1$-$C_{18}$ alkyl, $C_2$-$C_{18}$ alkenyl and $C_2$-$C_{18}$ alkynyl radicals, the said radicals being optionally substituted by a hydroxyl radical.

$R_1^{n+}$ is preferably chosen from alkali metal cations, especially sodium, ammonium, isopropylammonium, triethylammonium, trimethylammonium, tert-butylammonium and ethanolammonium, The molar quantity of formate employed relative to the disulphide is especially greater than 1 and more preferably between 1 and 5.

Sulphur dioxide may be present in catalytic quantity. The molar proportion of $SO_2$ relative to the formate is generally between 0.01 and 4, although the upper limit is not critical.

For a better application of the invention when the halide of formula II is liquid or solid, the molar quantity of the latter which is used relative to the disulphide is especially greater than or equal to 1 and preferably between 1 and 3.

When the halide of formula II is gaseous, as in the case of CF$_3$Br, the molar quantity of the latter which is used relative to the disulphide is especially greater than 1.

According to a first process for applying the invention, when a metal is employed, the latter is employed as a powder or as turnings and sulphur dioxide is advantageously introduced in gaseous form before the introduction of the halide of formula (II).

According to a second process for applying the invention, when an alkali metal dithionite is employed, the latter is introduced into the reactor as a saturated solution in water or formamide. It is even possible to introduce the dithionite in solid form. It is preferred to remove all the oxygen present in the reactor, and sulphur dioxide is then optionally introduced and the perhaloalkaline is introduced.

According to a third process for applying the invention, when a hydroxymethanesulphinate is employed, the latter is introduced in solid form directly into the reaction solvent.

Sulphur dioxide is optionally introduced, followed by the perhaloalkane.

According to a process for applying the invention, the disulphide is introduced in succession, followed by the formate, the solvent, the SO$_2$ in gaseous form and then the perhaloalkane.

At the end of reaction the solvent(s) and the reaction products are separated and the perhaloalkyl compound is then purified, for example, by extraction with the aid of solvents such as ethyl ether or petroleum ethers.

With regard to the reaction conditions, it is preferable to work at a temperature of between 20° and 100° C. or the boiling temperature of the solvent, and still more preferably when a dithionite is employed at a temperature of between 20° and 80° C.

In the preferred case of a gaseous halide such as CF$_3$Br it is nevertheless advantageous to produce the reaction in a solvent medium which dissolves the halide at least slightly at atmospheric pressure and much more so under pressure. This is the case, for example, using dimethylformamide for CF$_3$Br.

When the operation is carried out with a gas which is relatively insoluble in the reaction solvent, the reaction pressure is generally higher than 1 bar. A pressure of between 1 and 50 bars is preferred, although the upper limit is not an essential criterion, but merely a preference from the viewpoint of technology.

Thus, the reaction pressure is generally greater than 1 bar (pressure of the halide gas). From an industrial standpoint a pressure of between 1 and 50 bars is preferred, although the upper limit is not an essential criterion but merely a preference from the viewpoint of technology.

When the halide of formula II is gaseous, it is generally advantageous to conduct the reaction in subcritical pressure and temperature conditions.

The reactor should preferably not be made of a reactive material such as those described in the Patent Application published under number EP 165,135. The use of a glass reactor is thus preferred.

Among the products obtained by the process of the present invention there may be mentioned
trifluoromethylthiobenzene,
benzyl trifluoromethyl sulphide,
methyl trifluoromethyl sulphide,
methyl perfluorooctyl sulphide,
ethyl trifluoromethylthioacetate and
butyl perfluorobutyl sulphide,
4-trifluoromethylthio-3-cyano-5-amino-1-(2,6-dichloro-4-trifluoromethylphenyl)pyrazole.

The compounds which are the subject of the process of the invention are employed especially as synthesis intermediates in the pharmaceutical or plant-protection industry.

The starting disulphides are obtained in a known manner.

The invention will be described more completely with the aid of the following examples, which must not be considered as limiting the present invention.

EXAMPLE 1

The following are introduced into a thick glass flask: dimethylformamide (30 cc), water (15 cc), sodium dithionite (10 g), sodium hydrogen phosphate (10 g), phenyl disulphide (5.5 g), the flask is evacuated and is then thermostated at 20° C., the flask is then agitated for 6 hours at a bromotrifluoromethane pressure of between 5 and 2.5 atmospheres. Water (100 cc) is added and extraction is carried out with ether. After washing with 5% hydrochloric acid (2×20 ml) and then with 10% sodium carbonate, the ether phase is dried over magnesium sulphate. After evaporation of the solvent, trifluoromethylthiobenzene is obtained in 65% yield.

Bp: 77° C./20 mm Hg $_F=-42$ ppm

EXAMPLE 2

Dimethylformamide (30 cc), zinc (6.5 g), sulphur dioxide (4 g) and phenyl disulphide (5.5 g) are placed in the same flask as in Example 1. After reaction at 20° C. and the usual treatment, trifluoromethylthiobenzene is obtained.

EXAMPLE 3

Dimethylformamide (30 cc), water (2 g), sodium hydroxymethanesulphinate (15.5 g) and phenyldisulphide (5.5 g) are placed in the same flask as in Example 1. After reaction at 20° C. and the usual treatment, trifluoromethylthiobenzene is obtained in 93% yield.

EXAMPLE 4

Dimethylformamide (30 cc), water (2 g), zinc hydroxymethanesulphinate (13 g) and phenyl disulphide (5.5 g) are placed in the same flask as in Example 1. After reaction at 20° C. and the usual treatment, trifluoromethylthiobenzene is obtained.

EXAMPLE 5

Experiment 3 is repeated with ethyl dithioacetate (5.9 g) replacing the phenyl disulphide. After reaction at 20° C. and the usual treatment, ethyl trifluoromethylthioacetate is obtained in 55% yield.

Bp 71° C./100 mm Hg $_F=-41.7$ ppm $_H=4.27$ ppm (2H, q, 3.73 ppm (2H, s), 1.3 ppm (3H, t).

EXAMPLE 6

Experiment 5 is repeated with butyl disulphide (4.5 g) and butyl trifluoromethyl sulphide is obtained in 31% yield.

Bp 95° C. $_F=-41$ ppm $_H$(CH$_2$S) 2.7 ppm.

EXAMPLE 7

Perfluorobutyl iodide (3.5 g), sodium hydroxymethanesulphinate (4 g), benzyl disulphide (2.5 g) in dimethylformamide (10 cc) and water (0.5 cc) are stirred for 6 hours. After the usual treatment, benzyl perfluorobutyl sulphide is obtained, 17% yield.

Bp 92° C./17 mm Hg $F(CF_2S) = -88.8$ ppm $_H$7.3 ppm (5H, s) 4.2 ppm (2H, s).

EXAMPLE 8

Perfluorooctyl iodide (5.5 g), sodium dithionite (3 g), sodium hydrogen phosphate (3 g) and methyl disulphide (1 g) are stirred in dimethylformamide (10 cc) and water (5 cc) for 6 hours. After the usual treatment, methyl perfluorooctyl sulphide is obtained in 20% yield.

Bp 44° C./10 mm Hg $_H$: 2.4 ppm (s) $F(CF_2)$: $-92.3$ ppm.

EXAMPLE 9

Perfluorohexyl iodide (4.5 g), sodium hydroxymethanesulphinate (4 g) and phenyl disulphide (2.2 g) in dimethylformamide (10 cc) and water (0.5 cc) are stirred for 12 hours. After the usual treatment, phenyl perfluorohexyl sulphide is obtained in 40% yield.

$F(CF_2)$ $-87.2$ ppm Bp 99° C./18 mm Hg.

EXAMPLE 10

The phenyl disulphide in Example 9 is replaced with butyl disulphide (1.8 g); butyl perfluorohexyl sulphide is thus obtained in 22% yield.

$F = -86.3$ ppm $(SCF_2)$ $_H = 2.7$ ppm $(CH_2S)$.

EXAMPLE 11

The sodium hydroxymethanesulphinate in Example 10 is replaced with the zinc salt (3.5 g). The product is then obtained in 16% yield.

EXAMPLE 12

Experiment 3 is repeated, the bromotrifluoromethane being replaced with dichlorodifluoromethane. After reaction, chlorodifluoromethylthiobenzene is obtained.

EXAMPLE 13

Experiment 3 is repeated, the bromotrifluoromethane being replaced with bromochlorodifluoromethane at a pressure of 1.7 atmospheres. After reaction, chlorodifluoromethylbenzene is distilled off.

Bp 71° C./25 mm Hg $F = -27$ ppm 72% yield

EXAMPLE 14

Experiment 5 is repeated, the bromotrifluoromethane being replaced with bromochlorodifluoromethane. After reaction, ethyl chlorodifluoromethylthioacetate is obtained.

Bp 81° C./25 mm Hg $F = -27$ ppm$_H = 4.23$ ppm (2H, q, J=10.5 Hz) 3.75 ppm (2H, s) 1.3 ppm (3H, t) IR = 1718 cm$^{-1}$. 65% yield.

EXAMPLE 15

Preparation of
4-trifluoromethylthio-3-cyano-5-amino-1-(2,6-dichloro-4-trifluoromethylphenyl)pyrazole Firstly, 5-amino-3-cyano-1-(2,6-dichloro-4-trifluoromethylphenyl)-4-pyrazolyl disulphide (2 g) is dissolved in dimethylformamide (120 cc); secondly, sodium hydrogen phosphate 12H$_2$O (3.05 g) is dissolved in distilled water (60 cc). The dimethylformamide solution is then introduced into a 500-cm$^3$ Teflon-coated autoclave, followed by the aqueous solution. Sodium dithionite (1.48 g) is introduced in its turn with stirring. The autoclave is then closed and CF$_3$Br is introduced at a pressure of 12-13 bars (autogenous pressure).

After 2 h 30 min of good stirring (1,000 rev/min Rushton turbine) at 25° C., we obtained the following results:

DC=100%
RY determined (external standard HPLC) 75%.

EXAMPLE 16

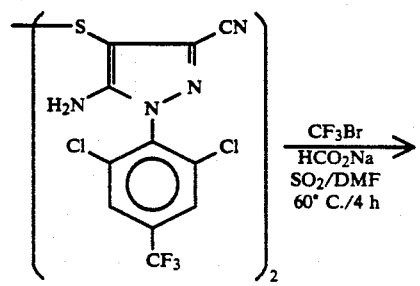

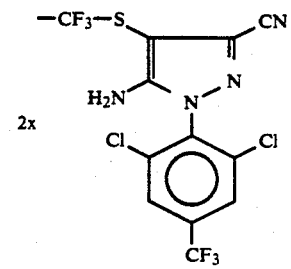

Pyrazole disulphide (4 g, 5.7 mmol), sodium formate (1.16 g, 17.1 mmol), DMF (20 cc) and SO$_2$ (1.45 g, 22.8 mmol) are introduced in succession into an autoclave.

This reaction mixture, well stirred, is heated to a temperature of 60° C. and a CF$_3$Br pressure of 13 bars is maintained for 4 h at this temperature. HPLC analysis of the reaction mixture produces the following results:

DC=95%
RY=90%

The disulphide is manufactured from 5-amino-3-cyano-1-(2,6-dichloro-4-trifluoromethylphenyl)-4-thiocyanatopyrazole obtained according to European Application No. 88/3,053,068, filed on 10 June 1988 in the name of May and Baker. A 50% strength aqueous NaOH solution (2 cc) is added to this product (3.0 g) in chloroform (40 cc).

The mixture is then treated with tribenzylammonium chloride (100 mg) and stirred at ambient temperature for 6 hours. The yellow solid is filtered off, dried, purified, eluted on a chromatography column with a dichloromethane-ethyl acetate (4:1) eluent, to produce a yellow solid, which is recrystallized from a hexane-toluene mixture to yield yellow crystals (1.59 g), m.p.: 303°-305° C.

EXAMPLE 17

Preparation of 1,2-dichloro-1,2,2-trifluoroethyl phenyl sulphide 1,1,2-Trichlorotrifluoroethane (3.8 g), phenyl disulphide (4.4 g), sodium dithionite (7 g) and sodium hydrogen phosphate (6 g) are stirred in dimethylformamide (20 cc) and water (10 cc) for 6 hours. After steam distillation and the usual treatment, 1,2-dichloro-1,2,2-trifluoroethyl phenyl sulphide (1.7 g) is obtained in 52% yield.

$\delta_F$: −6.3 ppm (2F, d, J=14.2 Hz) −89 ppm (t, 1F) and phenylthiotrifluoroethylene in 8% yield.

EXAMPLE 18

Preparation of dichlorofluoromethyl phenyl sulphide

The above experiment is repeated with trichlorofluoromethane (2.8 g); dichlorofluoromethyl phenyl sulphide (0.55 g) is obtained in 13% yield; $\delta_F$: −18.7 ppm (s).

EXAMPLE 19

Preparation of bromodifluoromethyl phenyl sulphide

The above experiment is repeated with bibromodifluoromethane (4.6 g); bromodifluoromethyl phenyl sulphide (0.3 g) is obtained in 6% yield; $\delta_F$: −19 ppm (s).

EXAMPLE 20

Preparation of 5-amino-4-(bromodifluoromethylthio)-3-cyano-1-(2,4,6-trichlorophenyl)-1H-pyrazole Part A:
5-amino-3-cyano-4-thiocyanato-1-(2,4,6-trichlorophenyl)-1H-pyrazole A solution of sodium thiocyanate (12.65 g, 0.156 mol) in methanol (62.5 cc) was subjected to magnetic stirring and was cooled to −65° C. in a carbon dioxide snow-acetone bath. A solution of bromine (8.31 g, 0.052 mol) in methanol (62.5 cc) was then added carefully to this mixture over a period of approximately 30 minutes, while the temperature was maintained in the range of −65° to −60° C. Finally, a suspension of 5-amino-3-cyano-1-(2,4,6-trichlorophenyl)-1H-pyrazole (15.0 g, 0.052 mol) in methanol (50 cc) was added portionwise to the mixture with stirring, while the temperature was maintained below −47° C. An additional portion of methanol (50 cc) was then added to rinse the pyrazole crystals remaining in the mixture. Cooling was then stopped and the reaction mixture was allowed to warm up to 18° C. over 3.3 hours, at the end of which time the mixture was stored in a refrigerator at 0° C. for a period of 16 hours. The reaction mixture was then allowed to warm up to room temperature over a period of 2.5 hours and was then poured, with stirring, into water (1,000 cc) to precipitate the product. The latter was collected by vacuum filtration, washed with water and dried in air. A dehydration was performed by dissolving in dichloromethane and placing in contact with MgSO$_4$. A filtration and a solvent removal by entrainment under vacuum then gave 5-amino-4-cyano-3-thiocyanato-1-(2,4,6-trichlorophenyl)-1H-pyrazole (16.2 g, 90.4%) in the form of a light-yellow coloured solid substance.

Analysis: $^1$H NMR (DMSO-d$_6$) δ7.19 (s, 2H), 7.95 (s, 2H) ppm.
IR (KBr) 2160, 2255 cm$^{-1}$.

Part B:
4,4'-dithiobis[5-amino-3-cyano-1(2,4,6-trichlorophenyl)-1H-pyrazole]

Benzyltriethylammonium chloride (0.32 g, 0.0014 mole) and a solution of NaOH (6.0 g, 0.15 mol) in water (20 cc) were added with stirring to a suspension of 5-amino-3-cyano-4-thiocyanato-1-(2,4,6-trichlorophenyl)-1H-pyrazole (16.2 g, 0.047 mol) in CHCl$_3$ (180 cc). The resulting mixture was stirred under laboratory atmosphere, at ambient temperature, for 3.1 hours, at the end of which time a TLC of a reaction aliquot portion showed that the reaction was complete. The yellow-coloured solid product was separated off by filtration, was washed with water, and was then dissolved in ethyl acetate, the solution being subjected to an extraction with water (2×200 ml) and to a dehydration over MgSO$_4$. A dehydration in a vacuum oven at a temperature of 70° to 75° C. for approximately 16 hours gave 4,4'-dithiobis[5-amino-3-cyano-1-(2,4,6-trichlorophenyl)-1H-pyrazole] (14.0 g, 93.5%) in the form of a yellow-coloured solid substance.

Analysis:
$^1$H NMR (DMSO-d$_6$) δ6.73 (s, 4H), 7.90 (s, 4H) ppm.
IR (KBr) 1496, 1550, 1625, 2245 cm$^{-1}$.

Part C:
5-amino-4-(bromodifluoromethylthio)-3-cyano-1-(2,4,6-trichlorophenyl)-1H-pyrazole Na$_2$S$_2$O$_4$ (0.42 g, 0.0024 mol) and Na$_2$HPO$_4$ (0.34 g, 0.0024 mol), followed by water (5 cc) and dibromodifluoromethane (1.01 g, 0.0048 mol) were added with stirring to a solution of 4,4'-dithiobis[5-amino-3-cyano-1-(2,4,6-trichlorophenyl)-1H-pyrazole] (1.0 g, 0.0016 mol) in DMF (10 cc). When the stirred mixture remained nonhomogeneous, an additional quantity of DMF (15 cc) and H$_2$O (5 cc) were added and the resulting rapid solution, containing a small quantity of semi-solid substance was then stirred at ambient temperature for 2.7 hours. The reaction mixture was then stirred with water (100 cc) plus ethyl ether (100 cc) and the ether phase was separated off, dehydrated over MgSO$_4$ and filtered. Removal of ether under vacuum gave a yellow-coloured oil (1.29 g) which was introduced into the top of a lightning chromatography column containing silica gel (65 g) and was eluted with dichloromethane, giving 5-amino-4-(bromodifluoromethylthio)-3-cyano-1-(2,4,6-trichlorophenyl)-1H-pyrazole (0.76 g, 52.8 %) in the form of a pale-yellow coloured solid substance, m.p. 163.5°–165° C.

Analysis: C$_{11}$H$_4$BrCl$_3$F$_2$N$_4$S;
Calculated: C, 29.46; H, 0.90; N, 12.49.
Found: C, 29.48; H, 0.90; N, 11.93.
Mass spectrum in IE mode: m/z 448 (parent with $^{33}$Cl$_2$$^{37}$Cl$^{79}$Br and $^{35}$Cl$_3$$^{81}$Br), 319 (parent $^{35}$Cl$_2$$^{37}$Br less CF$_2$$^{79}$Br).

EXAMPLE 21

Preparation of 5-amino-4-(bromochlorofluoromethylthio)-3cyano-1-(2,4,6-trichlorophenyl)-1H-pyrazole Na$_2$S$_2$O$_4$ (1.23 g, 0.0070 mol), Na$_2$HPO$_4$ (1.0 g, 0.0070 mol), water (30 cc) and, finally, chlorodibromofluoromethane (3.19 g, 0.0141 mol) were added with stirring to a mixture of 4,4'-dithiobis[5-amino-3-cyano-1-(2,4,6-trichlorophenyl)-1H-pyrazole] (3.0 g, 0.0047 mol) (prepared in part B above) and DMF (75 cc), and the resulting mixture was stirred at ambient temperature for 40 minutes. The reaction mixture was poured into water (300 cc) and the solution was subjected to a first extraction with ethyl ether (1×300 ml) and then with dichloromethane. A lightning chromatography on a column (silica gel) of the material obtained by subjecting the ether extract to a vacuum entrainment gave a relatively impure product (1.05 g) (fraction 13A). Removal of dichloromethane by vacuum evaporation gave a product fraction containing a large quantity of N,N-dimethylformamide (DMF). The latter was removed by rotary evaporation at a temperature of 90° to 100° C. over a period of 2.5 hours, under hard vacuum, the resulting residue being dissolved in dichloromethane and subjected to an extraction with water. Removal of the solvent from the dehydrated organic phase and a lightning chromatography on a column of silica gel then gave 5-amino-4-(bromochlorofluoromethylthio)-3-cyano-1-(2,4,6-trichlorophenyl)-1H-pyrazole (0.50 g) in the form of a bright yellow-coloured solid substance, m.p. 192°–193° C. The total product yield, including fraction 13A, was equal to 72%.

Analysis: $C_{11}H_4BrCl_4FN_4S$;
Calculated: C, 28.42; H, 0.87; N, 12.05.
Found: C, 28.63; H, 0.86; N, 11.92;
Mass spectrum in IE mode: m/z 464 (parent with $^{79}Br^{35}Cl_3^{37}Cl$ and $^{81}Br^{35}Cl_4$), 319 (parent $^{79}Br^{35}Cl_3^{37}Cl$ less $^{79}Br^{35}ClFC$).

EXAMPLE 22

Preparation of
5-amino-4-(bromochlorofluoromethylsulphinyl)-3-cyano-1-(2,4,6-trichlorophenyl)-1H-pyrazole and of
5-amino-4-(bromochlorofluoromethylsulphonyl)-3-cyano-1-(2,4,6-trichlorophenyl)-1H-pyrazole
5-amino-4-(bromochlorofluoromethylsulphinyl)-3-cyano-1-(2,4,6-trichlorophenyl)-1H-pyrazole A solution of 30% $H_2O_2$ (0.42 cc, 0.0041 mol) in trifluoroacetic acid (1 cc) was added with stirring and with cooling to 0° C. to a stirred mixture of 5-amino-4-(bromochlorofluoromethylthio)-3-cyano-1-(2,4,6-trichlorophenyl)-1H-pyrazole (1.05 g, 0.0023 mol), obtained in the form of fraction 13A in the above example, and trifluoroacetic acid (5 cc). The addition was carried out over a period of 5 minutes by means of a syringe inserted through a rubber septum which covered the mouth of the flask. Stirring was then continued, the ice bath being allowed to melt gradually, for a period of approximately 18 hours. The reaction mixture was poured into water (30 cc), the resulting solid substance being collected by filtration. The solid substance was dissolved in ethyl acetate and this solid was then washed with a 10% $NaHSO_3$ solution (2×25 cc), with brine (1×25 cc), a saturated $NaHCO_3$ solution (2×25 cc) and was then subjected to a final extraction with brine (2×25 cc). The organic phase was dehydrated ($MgSO_4$) and the solvent was then removed, giving a residue which was subjected to a lightning chromatography on a column of silica gel, the elution being carried out with dichloromethane. The desired sulphoxide was collected in the final fractions, which were combined, freed from solvent and dehydrated in a vacuum oven, giving 5-amino-4-(bromochlorofluoromethylsulphinyl)-3-cyano-1-(2,4,6-trichlorophenyl)-1H-pyrazole (0.39 g, 35.0%), m.p. 225°–226° C. with decomposition.

Analysis: $C_{11}H_4BRCl_4FN_4OS$;
Calculated: C, 27.47; H, 0.84; N, 11.65.
Found: C, 27.82; H, 0.86; N, 11.21.
Mass spectrum in IE mode: m/z 335 (parent $^{33}C_3^{37}Cl^{79}Br$ less $^{79}Br^{35}ClFC$).

5-Amino-4-(bromochlorofluoromethylsulphonyl)-3-cyano-1-(2,4,6-trichlorophenyl)-1H-pyrazole A new treatment of the above chromatography fractions obtained by the sulphoxide preparation described in the above example gave, after vacuum evaporation of the solvent, 5-amino-4-(bromochlorofluoromethylsulphonyl)-3-cyano-1-(2,4,6-trichlorophenyl)-1H-pyrazole (0.12 g, 10.5%), m.p. 251.5°–252.5° C. with decomposition.

Analysis: $C_{11}H_4BrCl_4FN_4O_2S$;
Calculated: C, 26.59, H, 0.81; N, 11.27.
Found: C, 26.99; H, 0.76; N, 11.13.

EXAMPLE 23

Preparation of
5-amino-4-(bromochlorofluoromethylthio)-3-cyano-1-[2,6-dichloro-4-(trifluoromethyl)phenyl]-1H-pyrazole $Na_2S_2O_4$ (1.92 g, 0.011 mol) and $Na_2HPO_4$ (1.56 g) were added to a stirred solution of 4,4-dithiobis[5-amino-3-cyano-1-[2,6-dichloro-4-(trifluoromethyl)phenyl]-1H-pyrazole] (5.11 g, 0.0073 mol) in DMF (115 cc), followed by water (45 cc), which resulted in a partial solution of the inorganic reactants. A portion of chlorodibromofluoromethane (4.96 g, 0.0219 mol) was then added, followed by an additional quantity of DMF (75 cc), resulting in a practically homogeneous mixture. The reaction mixture was stirred at ambient temperature for a period of 1.6 hours, and was then poured into water (450 cc) and this latter mixture was subjected to a careful extraction with a portion of ethyl ether (450 cc). The ether phase was separated off, dehydrated ($MgSO_4$) and the volatile substances were removed with a hard vacuum pump at its maximum output and at a bath temperature of 100° C. to remove practically all the DMF. The residue was subjected to a lightning chromatography on a column of silica gel, eluting with $CH_2Cl_2$, and the product collected was dehydrated under vacuum, giving 5-amino-4-(bromochlorofluoromethylthio)-3-cyano-1-[2,6-dichloro-4-(trifluoromethyl)phenyl]-1H-pyrazole (1.76 g, 24.2%), m.p. 191.5°–193° C.

Analysis: $C_{12}H_4BrCl_3F_4N_4S$;
Calculated: C, 28.91; H, 0.81; N, 11.24.
Found: C, 29.37; H, 0.75; N, 10.99.
Mass spectrum in IE mode: m/z 498 (parent with $^{35}Cl_2^{37}Cl^{79}Br$ and $^{35}Cl_3^{81}Br$), 351 (parent $^{35}Cl_2^{37}Cl^{79}Br$ less $^{37}Cl^{79}BrFC$).

EXAMPLE 24

Preparation of
5-amino-4-(bromodifluoromethylthio)-3-cyano-1-[2,6-dichloro-4-(trifluoromethyl)phenyl]-1H-pyrazole Sodium dithionite (0.78 cc) were added to a $Na_2HPO_4$ (0.64 g) and water (20 cc) were added to a stirred solution of 4,4′-dithiobis[5-amino-3-cyano-1-[2,6-dichloro-4-(trifluoromethyl)phenyl]-1H-pyrazole] (1.94 g, 0.003 mol) in DMF (45 cc). Only a partial solution was obtained and additional quantities of DMF (30 cc) and water (5 cc) were added, and this caused most of the solid substances to go into solution. Finally, $CF_2Br_2$ (1.89 g, 0.009 mol) was added and the resulting mixture was stirred at ambient temperature for a period of approximately 17 hours. The reaction mixture was poured into water (185 cc) and this mixture was subjected to a careful extraction with ethyl ether. The separated ether phase was dehydrated over $MgSO_4$ and all the volatile substances were removed by vacuum entrainment using a pump at maximum power, on a water bath at 100° C. for several hours. The resulting residue was subjected to a lightning chromatography on a column of silica gel, eluting with $CH_2Cl_2$, and the solvent was evaporated off, giving 5-amino-4-(bromodifluoromethylthio)-3-cyano-1[2,6-dichloro-4-(trifluoromethyl)phenyl]-1H-pyrazole (1.31 g, 90.0%) in the form of the white-coloured solid substance, m.p. 162.5°–163.5° C.

Analysis: $C_{12}H_4BrCl_2F_5N_4S$;
Calculated: C; 29.90; H, 0.84; N, 11.62.
Found: C, 30.03; H, 0.75; N, 11.39;
Mass spectrum in IE mode: m/z 482 (parent with $^{35}Cl_2{}^{81}Br$ and $^{35}Cl^{37}Cl^{79}Br$), 351 (parent $^{35}Cl_2{}^{81}Br$

EXAMPLE 25

Preparation of -5-Amino-3-cyano-4-dichlorofluoromethylthio-1-(2,6-dichloro-4-trifluoromethylphenyl) pyrazole Zinc powder (60 g) was added to a solution of bis [5-Amino-3-cyano-1-(2,6-dichloro-4-trifluoromethylphenyl) pyrazole-4-yl] disulphide (150 g) in dimethylformamide (1125 ml) and the mixture was stirred at ambient temperature. To this was added a solution containing sulphur dioxide (60.6 g) in dimethylformamide (160 g) followed by fluorotrichloromethane (290 g). After approximately 30 minutes a slight exotherm was noted (maximum temperature 30° C.). The reaction mixture was stirred at ambient temperature overnight. The mixture was filtered and added dropwise over 2 hours to ice/water (14 l). The resultant solid was collected, washed thoroughly with water and dried to yield a yellow/orange solid (185 g). Recrystallisation from toluene/hexane yielded the title compound in pure form (123 g, 64%) m.p.; 187°–189° C.

EXAMPLE 26

Preparation of -5-Amino-3-cyano-4-dichlorofluoromethylthio-1-(2,6-dichloro-4-trifluoromethylphenyl) pyrazole

| | |
|---|---|
| (5.7 mmole) | 4 g |
| Dimethylformamide | 178 ml |
| Water | 89 ml |
| Sodium Phosphate, dibasic | 3.23 g |
| Fluorotrichloromethane | 3.90 g |
| Sodium Dithionite (>85%) | 3.96 g |

Sodium phosphate, dibasic (3.23 g) was dissolved in a mixture of dimethylformamide (178 ml) and water (78 ml) with stirring at 16° C. To this was added in order:
1) Bis-[5-amino-3-cyano-1-(2,6-dichloro-4-trifluoromethylphenyl)-pyrazo-4-yl]-disulphide(4 g, 5.7 mmole)
2) Fluorotrichloromethane (3.9 g)
3) Sodium dithionite (3.96 g)

This was stirred at 15°–17° C. for 1 hour and was then poured into iced-water (1600 ml), stirred for ½ hour and then the white solid filtered, washed with water (800 ml) and then dried.

m.p. 190°–193° C., Yield: 4.34 g (84.1%)

We claim:
1. A process for the preparation of perhaloalkylthioethers which comprises bringing into contact, optionally in a solvent:

(1) a reducing agent comprising a metal selected from the group consisting of zinc, cadmium, aluminium and manganese, with sulphur dioxide,
(2) a disulphide, and
(3) a perfluoroalkyl halide.

2. The process according to claim 1, wherein the perfluoroalkyl halide has the formula $$XCFYT \qquad (II)$$

wherein Y and T are independently of each other a halogen atom selected from the group consisting of fluorine, chlorine and bromine, or a $C_1$–$C_{11}$ perhaloalkyl chain, and X is a halogen atom selected from the group consisting of chlorine, bromine and iodine.

3. The process according to claim 2, wherein when X is bromine, then Y and T are fluorine, and when X is iodine, then Y is a perfluoroalkyl chain and T is fluorine.

4. The process according to claim 3, wherein the disulphide has the formula $$R-S-S-R$$

wherein R is a hydrocarbyl radical.

5. The process according to claim 4, wherein the hydrocarbyl radical R is:
(a) a linear or branched carboacyclic (aliphatic) radical, said radical being saturated or having one to five ethylenic or acetylenic unsaturations, or
(b) a carbocyclic or heterocyclic radical selected from the group consisting of (i) an aromatic or nonaromatic monocyclic system, (ii) an aromatic or nonaromatic bicyclic system, (iii) an aromatic or nonaromatic polycyclic system, and (iv) a bridged system.

6. The process according to claim 4, wherein the hydrocarbyl radical R is:
(a) a saturated linear or branched carboacyclic (aliphatic) radical, or
(b) a carbocyclic or heterocyclic radical selected from the group consisting of (i) ana aromatic or saturated nonaromatic monocyclic system, (ii) an aromatic or saturated nonaromatic bicyclic system, (iii) an aromatic or saturated nonaromatic polycyclic system, and (iv) a saturated bridged system.

7. The process according to claim 4, wherein the hydrocarbyl radical R is a phenyl radical, optionally bearing one or more substituents selected from the group consisting of:
halogen atoms (I, Cl, Br, F);
$C_6$–$C_{10}$ aryl radicals, optionally bearing 1 to 6 substituents selected from the group consisting of halogen atoms (I, Cl, Br, F), $C_1$–$C_6$ alkyl radicals, $C_1$–$C_6$ alkoxy radicals, polyhalo-$C_1$–$C_6$ alkyl radicals and polyhalo-$C_1$–$C_6$ alkoxy radicals;
$C_1$–$C_9$ heteroalkyl radicals, additionally containing 1 to 4 heteroatoms selected from the group consisting of nitrogen, sulphur and oxygen, said radicals optionally bearing one of the substituents defined above for the $C_6$–$C_{10}$ aryl radicals;
$C_1$–$C_6$ alkoxy radicals;
polyhalo-$C_1$–$C_6$-alkoxy radicals;
$C_1$–$C_6$ alkyl radicals; and
$C_1$–$C_6$ polyhaloalkyl radicals;
or wherein the hydrocarbyl radical R is an alkyl radical, optionally bearing one or more substituents selected from the group consisting of:

halogen atoms (I, Cl, Br, F);

$C_6$-$C_{10}$ aryl radicals, optionally bearing 1 to 6 substituents selected from the group consisting of halogen atoms (I, Cl, Br, F), $C_1$-$C_6$ alkyl radicals, $C_1$-$C_6$ alkoxy radicals, polyhalo-$C_1$-$C_6$-alkyl radicals and polyhalo-$C_1$-$C_6$-alkoxy radicals;

$C_1$-$C_9$ heteroalkyl radicals, additionally containing 1 to 4 heteroatoms selected from the group consisting of nitrogen, sulphur and oxygen, said radicals optionally bearing one of the substituents defined above for the $C_6$-$C_{10}$ aryl radicals;

$C_1$-$C_6$ alkoxy radicals; and polyhalo-$C_1$-$C_6$-alkoxy radicals;

or wherein the hydrocarbyl radical R has the formula

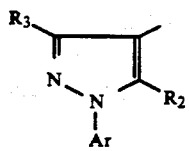

wherein $R_2$ is an —$NR_4R_5$ amino group in which $R_4$ and $R_5$, which are identical or different, are selected from the group consisting of a hydrogen atom; a $C_1$-$C_6$ alkyl radical, optionally substituted by a $C_2$-$C_5$ alkoxycarbonyl radical; a $C_3$-$C_6$ cycloalkyl radical; a $C_2$-$C_7$ alkanoyl radical, optionally forming a cyclic imide group of 5 to 6 atoms together with the nitrogen atom to which $R_4$ and $R_5$ are attached, said imide group being optionally substituted by one to six halogen atoms; a $C_2$-$C_7$-alkoxycarbonyl radical; and a polyhalo-$C_2$-$C_7$-alkoxycarbonyl radical; or $R_2$ is a $C_1$-$C_4$ alkylsulphinyl radical; a $C_2$-$C_5$ alkoxymethylene radical, optionally substituted on the methylene by a $C_1$-$C_4$ alkyl radical; a halogen atom; a $C_1$-$C_6$ alkyl radical; a carboxy radical; a $C_1$-$C_6$ alkylthio radical; a polyhalo-$C_1$-$C_6$-alkylthio radical; a $C_1$-$C_6$ alkylsulphinyl radical; a polyhalo-$C_1$-$C_6$-alkylsulphinyl radical; a $C_1$-$C_6$ alkylsulphonyl radical; a polyhalo-$C_1$-$C_6$-alkylsulphonyl radical; a tri($C_1$-$C_6$-alkyl)silylmethyl radical; a tri($C_1$-$C_6$)silyl radical; or a cyano radical; or $R_2$ is an HN—C(—=A)—$R_6$ residue, wherein:

$R_6$ is a hydrogen atom, a $C_1$-$C_6$ alkyl radical; a $C_1$-$C_4$ alkenyl radical; $C_1$-$C_4$ alkynyl radical; $C_1$-$C_4$ alkoxyalkyl radical; a $C_1$-$C_4$ alkylthioalkyl radical, a $C_1$-$C_4$ alkoxy radical; a $C_1$-$C_4$ alkylthio radical, a $C_1$-$C_4$ alkylamino radical, a di($C_1$-$C_4$-alkyl)amino radical; a polyhalo-$C_1$-$C_4$-alkyl radical; a $C_3$-$C_7$ cycloalkyl radical, optionally substituted by one or more halogen atoms or a $C_1$-$C_4$ alkyl radical; or a $C_1$-$C_4$ haloalkyl radical; or $R_6$ is a phenyl radical; a phenylthio radical; a phenoxy radical; or a phenylamino radical, these phenyl nuclei being optionally substituted by cyano, $C_1$-$C_4$ alkyl, $C_1$-$C_4$ alkoxy, $C_1$-$C_4$ alkylthio; $C_1$-$C_4$ alkylsulphinyl; $C_1$-$C_4$ alkylsulphonyl; polyhalo-$C_1$-$C_4$-alkyl, polyhalo-$C_1$-$C_4$-alkoxy; polyhalo-$C_1$-$C_4$-alkylthio; polyhalo-$C_1$-$C_4$-alkylsulphinyl; polyhalo-$C_1$-$C_4$-alkylsulphonyl; or halogen;

A is a sulphur or oxygen atom;

$R_3$ is a halogen atom, a cyano radical, a $C_1$-$C_6$ alkyl radical, a polyhalo-$C_1$-$C_6$-alkyl radical or a $C_3$-$C_6$ cycloalkyl radical; and Ar is a phenyl or pyridyl nucleus, optionally bearing 1 to 4 substituents selected from the group consisting of cyano, $C_1$-$C_4$ alkyl, $C_1$-$C_4$ alkoxy, $C_1$-$C_4$ alkylthio, $C_1$-$C_4$ alkylsulphinyl, $C_1$-$C_4$ alkylsulphonyl, polyhalo-$C_1$-$C_4$-alkyl, polyhalo-$C_1$-$C_4$-alkoxy, polyhalo-$C_1$-$C_4$-alkylthio, polyhalo-$C_1$-$C_4$-alkylsulphinyl, polyhalo-$C_1$-$C_4$-alkylsulphonyl and halogen.

8. The process according to claim 7, wherein the hydrocarbyl radical R is a phenyl radical, optionally bearing one or more substituents selected from the group consisting of:

halogen atoms (I, Cl, Br, F);

$C_6$-$C_{10}$ aryl radicals, optionally bearing 1 to 6 substituents selected from the group consisting of halogen atoms (I, Cl, Br, F), $C_1$-$C_6$ alkyl radicals, $C_1$-$C_6$ alkoxy radicals, polyhalo-$C_1$-$C_6$ alkyl radicals and polyhalo-$C_1$-$C_6$ alkoxy radicals;

$C_1$-$C_9$ heteroalkyl radicals, additionally containing 1 to 4 heteroatoms selected from the group consisting of nitrogen, sulphur and oxygen, said radicals optionally bearing one of the substituents defined above for the $C_6$-$C_{10}$ aryl radicals;

$C_1$-$C_6$ alkoxy radicals;

polyhalo-$C_1$-$C_6$-alkoxy radicals;

$C_1$-$C_6$ alkyl radicals; and $C_1$-$C_6$ polyhaloalkyl radicals.

9. The process according to claim 8, wherein the hydrocarbyl radical R is an unsubstituted phenyl radical.

10. The process according to claim 7, wherein the hydrocarbyl radical R has the formula

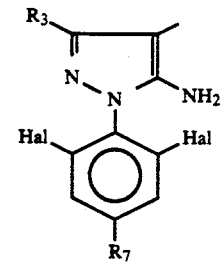

where $R_3$ is as defined in claim 7, Hal is a fluorine, bromine or chlorine atom or a hydrogen atom, and $R_7$ is a trifluoromethyl or trifluoromethoxy group.

11. The process according to claim 1, wherein the reaction is carried out in an aprotic and sufficiently polar solvent selected from the group consisting of formamide, dimethylformamide, dimethylacetamide, hexamethylphosphoramide, N-methylpyrrolidone, dimethyl sulphoxide, sulpholane, dioxane, tetrahydrofuran and dimethoxyethane.

12. The process according to claim 1, wherein the metal employed is zinc.

13. The process according to claim 12, wherein the molar quantity of zinc is greater than one relative to the disulphide.

14. The process according to claim 2, wherein the molar quantity of halide of formula (II) which is used is greater than one relative to the disulphide.

15. The process according to claim 1, wherein, when the perfluoroalkyl halide is in the gaseous state, the reaction is carried out in a solvent which dissolves the gas under a pressure of the latter which is lower than about 50 bars.

16. The process according to claim 1, wherein the reaction temperature is between 20° C. and 100° C. or at the boiling point of the solvent.

* * * * *